United States Patent [19]
Bobrow

[11] Patent Number: 5,863,748
[45] Date of Patent: Jan. 26, 1999

[54] P-HYDROXYCINNAMOYL-CONTAINING SUBSTRATES FOR AN ANALYTE DEPENDENT ENZYME ACTIVATION SYSTEM

[75] Inventor: Mark Norman Bobrow, Lexington, Mass.

[73] Assignee: New Life Science Products, Inc., Boston, Mass.

[21] Appl. No.: 818,161

[22] Filed: Mar. 14, 1997

[51] Int. Cl.$^6$ ...................................................... C12Q 1/28
[52] U.S. Cl. ............................ 435/28; 435/7.91; 435/188
[58] Field of Search ..................................... 435/7.9, 7.91, 435/7.92, 28, 188, 810; 436/501, 518

[56] References Cited

U.S. PATENT DOCUMENTS 5,182,203  1/1993  Ebersole et al. ........................ 435/196
5,196,306  3/1993  Bobrow et al. .......................... 435/7.9
5,583,001  12/1996 Bobrow et al. .......................... 435/7.5

FOREIGN PATENT DOCUMENTS 7308200  5/1994  Japan .

OTHER PUBLICATIONS

Mehta D., Synthesis and Biological Screening of Some New 2–Pyrazolines, Cyanopyridines and Benzodiazepines, Indian J of Heterocyclic Chemistry, vol. 6, 271–276, Apr. 1997.

*Primary Examiner*—Ralph Gitomer
*Attorney, Agent, or Firm*—Gifford, Krass, Groh, Sprinkle, Patmore, Anderson & Citkowski, P.C.

[57]  ABSTRACT

The present invention concerns novel p-hydroxycinnamoyl-containing substrates which can be used in catalyzed reporter deposition to amplify the detector signal and improve assay detection limits.

16 Claims, 1 Drawing Sheet

P-HYDROXYCINNAMOYL-CONTAINING SUBSTRATES FOR AN ANALYTE DEPENDENT ENZYME ACTIVATION SYSTEM

FIELD OF THE INVENTION

This invention relates to novel peroxidase substrates, and more particularly, to cinnamoyl-containing substrates which can be used in a variety of applications such as catalyzed reporter deposition.

BACKGROUND OF THE INVENTION

Peroxidase, because of its high turnover rate, good stability, and availability is widely used in enzyme-based analytical methods. For example, horseradish peroxidase (HRP) (EC 1.11.1.7) catalyzes the oxidation of a large variety of hydrogen-donating substrates with hydrogen peroxide. HRP is also one of the preferred enzymes for use in catalyzed reporter deposition.

Catalyzed reporter deposition is a novel method of signal amplification which constitutes the subject matter of U.S. Pat. Nos. 5,196,306 and 5,583,001. It is also discussed in Bobrow et al., Journal of Immunological Methods, 125: 279–285 (1989) and in Bobrow et al., Journal of Immunological Methods, 137: 103–112(1991).

The method utilizes an analyte-dependent enzyme activation ("ADEAS") to catalyze the deposition of additional reporter enzyme onto the solid phase, resulting in signal amplification and improved assay detection limits. In a preferred embodiment, HRP is the ADEAS.

The ADEAS reacts with a conjugate consisting of a detectably labeled substrate specific for the ADEAS. When the ADEAS and the conjugate react, an activated conjugate is formed which deposits covalently wherever receptor for the activated conjugate is immobilized. The receptor is not reactive with the analyte-dependent enzyme activation system.

Conjugates can be synthesized using conventional coupling and labeling techniques. Substrate choice will depend upon the ADEAS selected. Thus, detailed knowledge is required of the catalytic properties of each specific enzyme in order to properly design a useful synthetic substrate and, if necessary, a receptor. Examples of conjugates which have been described include substituted phenols such as biotin tyramine, fluorescein tyramine, NADP, phosphorylated biotin, etc.

However, care must be exercised in designing substrates suitable for peroxidase-mediated assays. Guilbault et al., Analytical Chemistry, Vol. 40, No. 8, pages 1256–1263 (1968) studied a wide variety substrates for fluorometric determination of oxidative enzymes such as peroxidase, galactose oxidase, glucose oxidase, and invertase. These researchers reported that 3,4-dihydroxycinnamic acid, which contains a double bond in the side chain was not a useful substrate for the fluorometric determination of oxidative enzymes because it stopped the reaction with the enzyme.

SUMMARY OF THE INVENTION

The present invention concerns a p-hydroxycinnamoyl-containing compound having the structure:

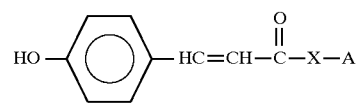

wherein:
X is a linker group, capable of linking A to a p-hydroxycinnamoyl moiety, and
A is a detectable label.

In another embodiment the invention concerns the use of such cinnamoyl-containing compounds in assays for detecting or quantitating the presence or absence of an analyte in a sample in which catalyzed reporter deposition is used to amplify the reporter signal.

BRIEF DESCRIPTION OF THE FIGURES

The file of this patent contains at least one drawing executed in color.

DETAILED DESCRIPTION OF THE INVENTION

Figure 1:
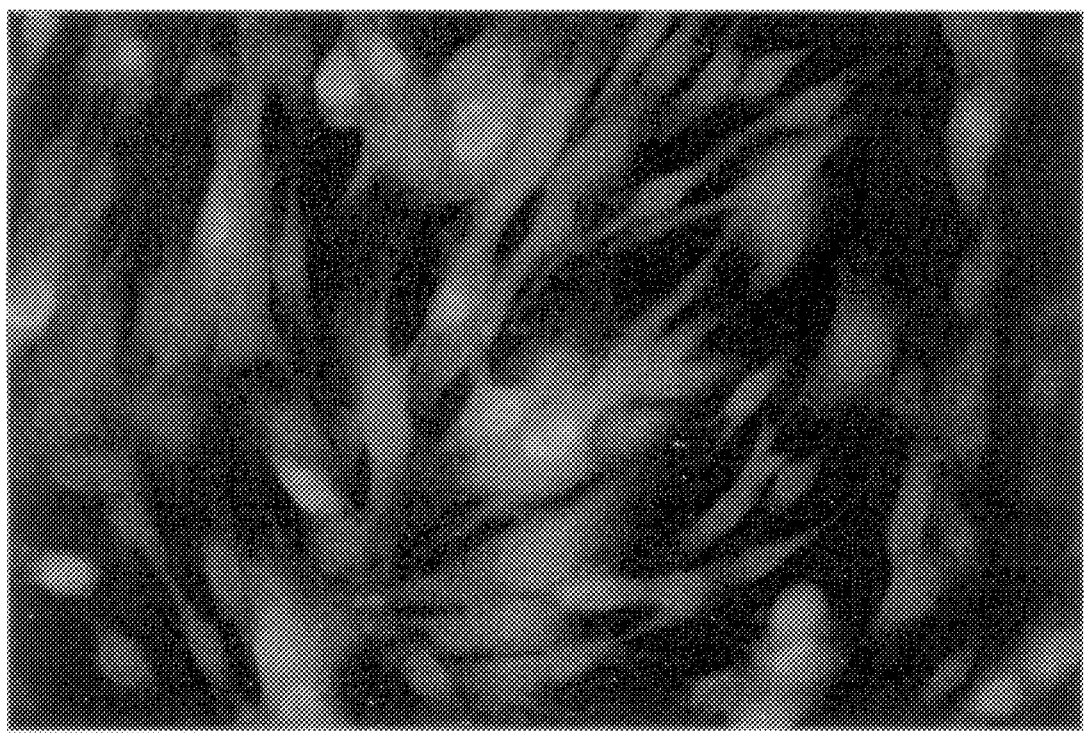
FIG. 1 shows detection of cytomegalovirus early antigen using catalyzed reporter deposition to amplify the detector signal. HRP was the ADEAS and biotin tyramide was the conjugate.

The term analyte dependent enzyme activation system (ADEAS) refers to an enzyme system wherein (i) at least one enzyme is coupled, in any manner known to those skilled in the art, to a member of a specific binding pair, or (ii) the enzyme need not be coupled to a member of a specific binding pair when it is the analyte. The enzyme, either by itself or in connection with a second enzyme, catalyzes the formation of an activated conjugate which then is deposited wherever there is a receptor for the activated conjugate.

The term amplification as used herein means amplification of reporter signal due to deposition of a conjugate activated by an ADEAS.

The term conjugate as used herein means a detectably labeled cinnamoyl-containing substrate specific for a peroxidase-mediated ADEAS whether it be a single enzyme ADEAS or multi-enzyme ADEAS conjugate as is discussed below.

The term detectably labeled means that the substrate can be coupled to either a reporter or to an unlabeled first member of a specific binding pair provided that the reporter introduces a different moiety to the substrate as is discussed below. When the substrate is coupled to an unlabeled member of a specific binding pair, following binding to the receptor, the substrate-specific binding partner complex is reacted with the second member of the binding pair which is coupled to a reporter. Alternately, the substrate-specific binding partner complex can be pre-reacted with the detectably labeled other member of the specific binding pair prior to deposition.

The term deposition means directed binding of an activated conjugate to the receptor which results from the formation of a specific binding pair interaction as described below.

The term receptor means a site which will bind to the activated conjugate through the formation of a specific binding pair interaction as described below.

The term activated conjugate means that the conjugate has been primed by the ADEAS to bind with the receptor.

The ADEAS catalyzes deposition of a conjugate (i.e., a detectably labeled substrate specific for the ADEAS) by converting the substrate portion of the conjugate to an activated form which binds covalently wherever there is a receptor. The ADEAS does not utilize enzyme cascade reactions or enzyme cycling to effect amplification. Rather, it uses either a single enzyme or combination of enzymes to activate the conjugate. Deposition of conjugate occurs only if the analyte and ADEAS have been reacted and a receptor is available to bind the activated conjugate. Thus, the ADEAS, conjugate and receptor are chosen to form an operational trio. The analyte and the ADEAS can be the same if the analyte is an enzyme (e.g., peroxidase) or different.

The instant invention concerns novel cinnamoyl-containing substrates which heretofore were thought to be unsuitable substrates for peroxidase-mediated reactions because it would be expected that such cinnamoyl-containing substrates would inhibit the reaction with the enzyme.

ADEAS' suitable for use with the cinnamoyl-containing substrates of the invention include oxidoreductases. More particularly, peroxidases can be mentioned. The preferred ADEAS which is suitable for the novel substrates of the invention is horseradish peroxidase.

It has been found, surprisingly and unexpectedly, that a novel conjugate having a p-hydroxycinnamoyl moiety in its structure significantly improves the sensitivity of catalyzed reporter deposition at least ten-fold beyond the level currently achieved using non-cinnamoyl containing conjugates.

The novel p-hydroxycinnamoyl-containing compounds of the invention have the structure:

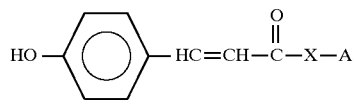

wherein

X is a linker group, capable of linking A to a p-hydroxycinnamoyl moiety, and

A is a detectable label.

The linker group can be virtually any linker group capable of linking the detectable label to the p-hydroxycinnamoyl moiety. Many linker groups attached to a detectable label are commercially available. Examples of linker groups not attached to a detectable label include the following:

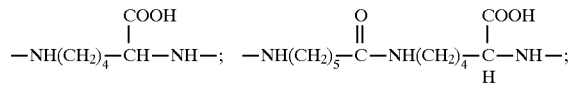

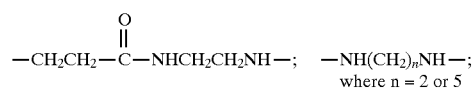

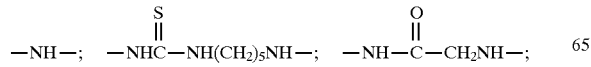

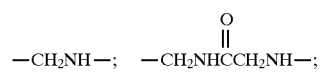

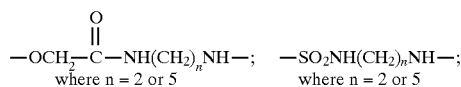

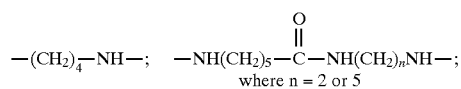

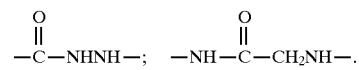

Examples of linker groups attached to detectable labels include the following:

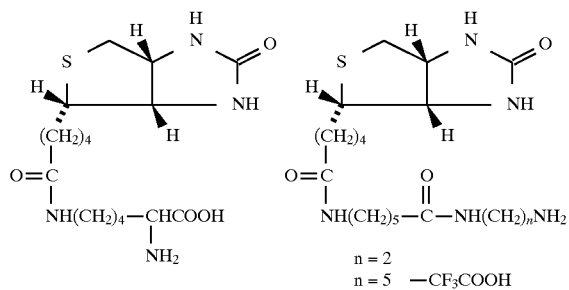

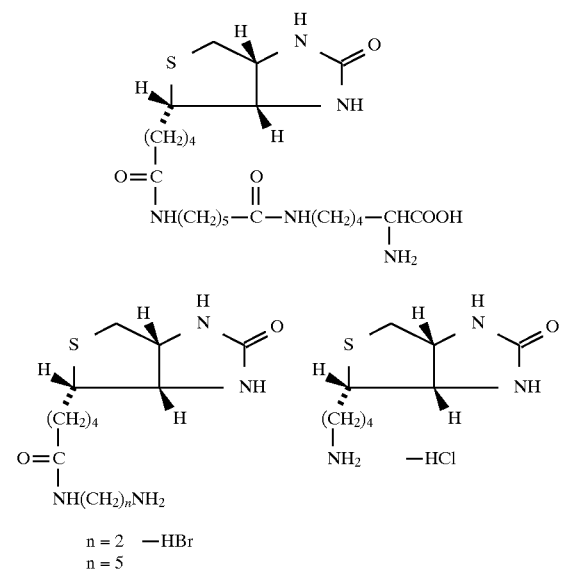

-continued

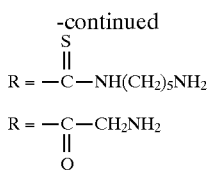

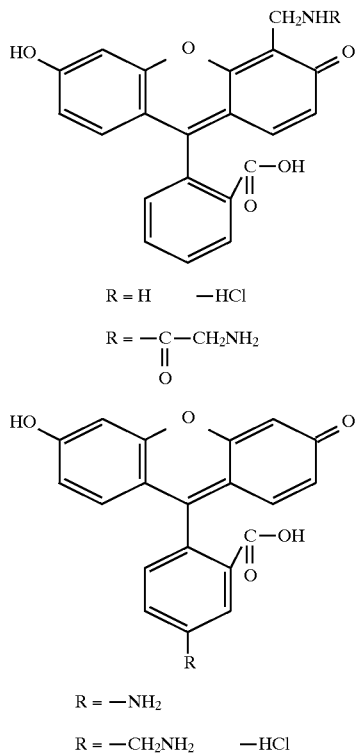

A wide variety of reporters are available for coupling to the substrate to produce the conjugate or to couple to a member of a specific binding pair. Reporters can be a radioactive isotope such as $^{125}I$, enzymes, fluorogenic, chemiluminescent, or electrochemical materials.

Examples of reporter enzymes which can be used to practice the invention include hydrolases, lyases, oxidoreductases, transferases, isomerases and ligases. Some preferred examples are phosphatases, esterases, glycosidases and peroxidases. Specific examples include alkaline phosphatase, lipases, beta-galactosidase and horseradish peroxidase. As was noted above, if an enzyme is used as a reporter, it can be the same as or different from the enzyme or enzymes used in the ADEAS. The present invention can be used to catalyze deposition of a radioisotopically labeled conjugate or an enzyme-labeled conjugate, etc.

If the reporter is a member of a specific binding pair, then it can be of the immune or the non-immune type. Immune specific binding pairs are exemplified by antigen/antibody systems or hapten/antihapten systems. The antibody member, whether polyclonal, monoclonal or an immunoreactive fragment thereof, can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')$_2$ frag,emts, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc.

The compounds of the invention can be synthesized using conventional coupling and labeling techniques as illustrated in the examples below. One approach can be to react p-hydroxycinnamic acid according to the following scheme:

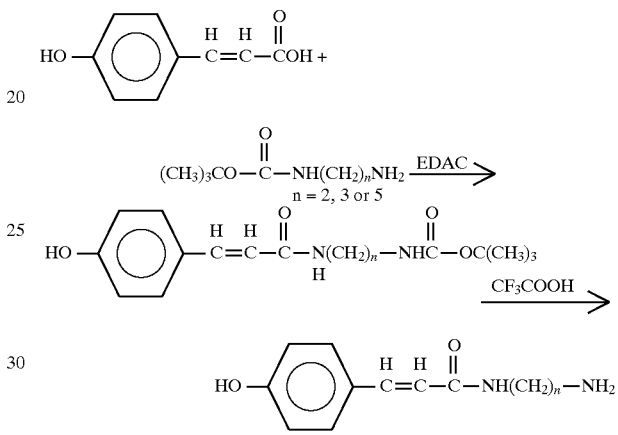

The resulting amine can then be reacted with suitable labels containing N-hydroxysuccinimide or isothiocyanate moieties to produce the final p-hydroxycinnamoyl-containing compound.

As was noted above, many linker groups attached to detectable labels are commercially available. These commercially available linker groups can be reacted with p-hydroxycinnamic acid using conventional protocols well known to those skilled in the art.

When a detectably labeled p-hydroxycinnamoyl-containing compound (conjugate) of the invention is activated, it will bind wherever there is a receptor. The activated conjugate binds to the receptor via a specific binding pair interaction which in this case is a covalent bond. An exogenous receptor means a receptor which does not originate within the assay. It can be immobilized on the surface of a support prior to adding the conjugate to the reaction mixture. An endogenous receptor means a receptor which originates within the assay. It is believed that the novel conjugates of the invention, when activated, bind with receptors suitable for activated phenolic moieties such as electron rich moieties.

In another embodiment, this invention concerns the use of these detectably labeled cinnamoyl-containing compounds in assays for detecting or quantitating the presence or absence of an analyte in a sample using catalyzed reporter deposition to amplify the reporter signal. Virtually any assay format such as an immunoassay or a nucleic acid hybridization assay can be used.

It should be clear to those skilled in the art that a large number of variations are possible and all these variations fall within the scope of the invention.

The following examples are intended to illustrate the invention and should not be construed as limitations thereon.

EXAMPLE 1

4-Hydroxycinnamic acid, N-hydroxysuccinimide ester

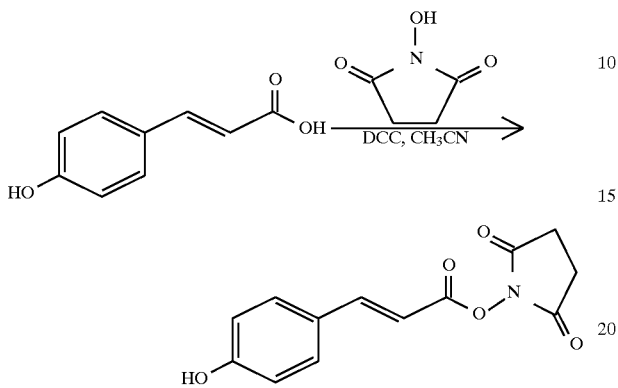

p-Hydroxycinnamic acid (5.0 g, 30.5 mmol) is dissolved in acetonitrile (150 mL) with warming followed by the addition of N-hydroxysuccinimide (4.0 g, 35 mmol) and 1,3-dicyclohexylcarbodiimide (1M in dichloromethane, 35 mL, 35 mmol). The pale yellow solution is stirred at room temperature overnight, filtered, and the filtrate is evaporated and purified by silica gel chromatography, eluting with 1:1 ethyl acetate:hexane. Fractions containing product by thin layer chromatography are pooled and evaporated to give a white solid (3.31 g, 42%). $^1$H NMR (DMSO-$d_6$) $\delta$7.9 (d, 1H, vinyl), 7.7 (d, 2H, phenyl 3,5), 6.9 (d, 2H, phenyl 2,6), 6.7 (d, 1H, vinyl), 2.8 (s, 4H, succinimide methylene).

EXAMPLE 2

N-1-Biotinyl-N-2-(4-hydroxycinnamoyl)-ethane diamine

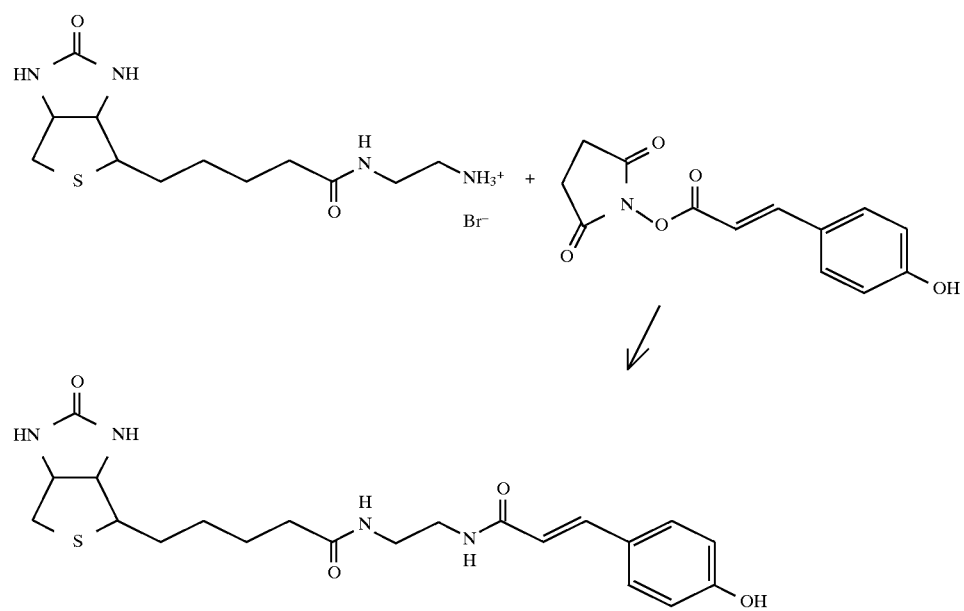

N-(2-aminoethyl)biotinamide hydrobromide (25 mg, 0.068 mmol), triethylamine (10 µL, 0.072 mmol), and 4-hydroxycinnamic acid, succinimidyl ester (18 mg, 0.068 mmol) are dissolved in dimethylformamide (DMF) (1 mL) and stirred overnight at room temperature. The reaction mixture is purified by C18 reverse phase chromatography, eluting with a linear gradient of 0–100% methanol in water over 30 minutes. The peak eluting at 22 minutes is collected and evaporated to give 22 mg of a white solid (0.051 mmol, 75%). $^1$H NMR (CD$_3$OD) $\delta$7.5 (d, 1H, vinyl), 7.4 (d, 2H, aromatic 3,5), 6.8 (d, 2H, aromatic 2,6), 6.4 (d, 1H, vinyl), 4.4 (m, 1H, biotin methine-NH), 4.2 (m, 1H, biotin methine-NH), 3.4 (m, 4H, ethane diamide), 3.1 (m, 1H, biotin methine-S), 2.8 (1H, biotin methylene-S), 2.6 (1H, biotin methylene-S), 2.2 (2H, biotin $CH_2$-CO), 1.3–1.7 (m, 6H, biotin aliphatics).

EXAMPLE 3

N-ε-(2,4-Dinitrophenyl)-N-α-(4-Hydroxcinnamoyl)-L-Lysine

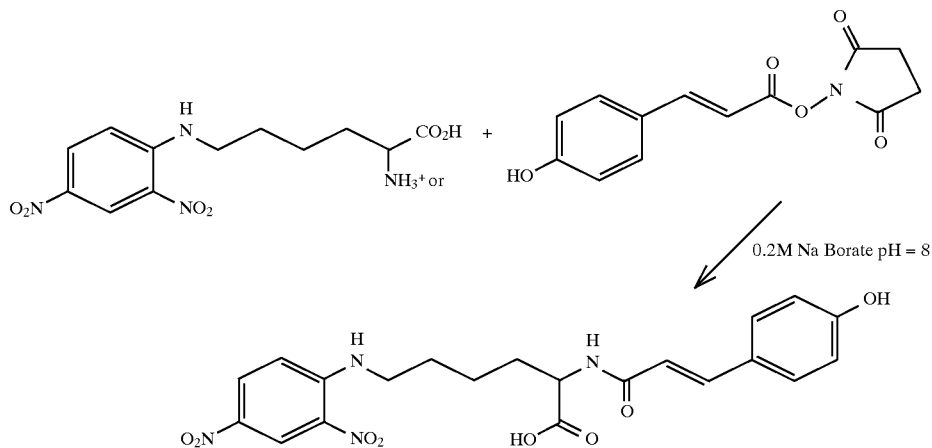

N-ε-(2,4-Dinitrophenyl)-L-lysine (32 mg, 0.09 mmol) is suspended in 0.2 M sodium borate (3 mL) pH=8, and a solution of 4-hydroxycinnamic acid, succinimidyl ester (35 mg, 0.13 mmol) in DMF (0.5 mL) is added in small portions with stirring. The yellow suspension is stirred at room temperature overnight and the crude reaction mixture is purified by C18 reverse phase chromatography, eluting with a linear gradient of 50–100% methanol in 50 mM sodium phosphate, pH=3 over 15 minutes. The major peak eluting at approximately 11 minutes is pooled from several injections, desalted on a C8 sep-pak cartridge, and evaporated to give 10 mg of a yellow solid (0.02 mmol, 25%). $^1$H NMR ($CD_3OD$) δ8.9 (s, 1H, DNP H-3), 8.2 (d, 1H, DNP H-5), 7.4 (d, 1H, vinyl), 7.3 (d, 2H), 7.2 (d, 1H, DNP H-6), 6.8 (d, 2H, aromatic 2,6), 6.4 (d, 1H, vinyl), 4.5 (m, 1H, lysine methine), 3.5 (t, 2H, $CH_2$-NH), 2.1–1.5 (m, 6H, $CH_2$).

EXAMPLE 4

DAMP-Cinnamate

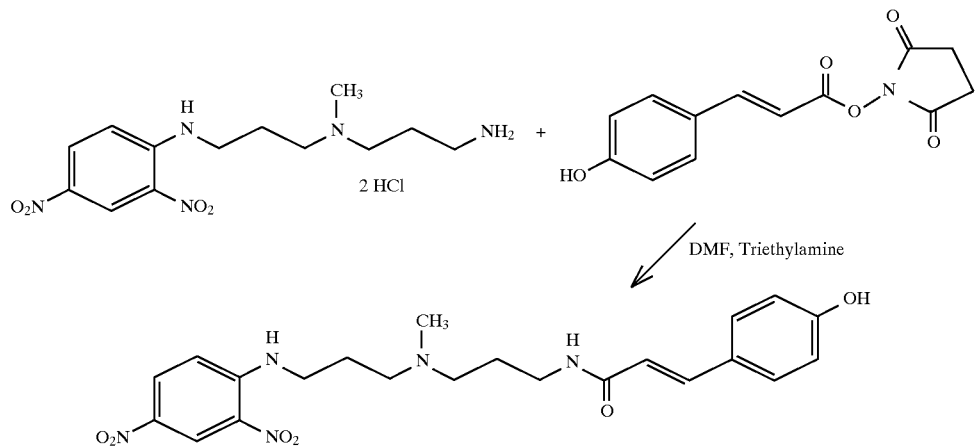

N-(3-((2,4-Dinitrophenyl)amino)propyl)-N-(3-aminopropyl)methylamine, dihydrochloride (DAMP) (45 mg, 0.12 mmol), triethylamine (35 μL, 0.25 mmol), and 4-hydroxycinnamic acid, succinimidyl ester (35 mg, 0.13 mmol) are dissolved in dimethylformamide (DMF) (1 mL) and stirred overnight at room temperature. The reaction mixture is evaporated in vacuo, dissolved in a minimum amount of methanol/water, and purified by C8 reverse phase chromatography, eluting with a linear gradient of 0–100% methanol in water over 30 minutes. The first major peak is collected and evaporated to give 27 mg of a yellow solid (0.06 mmol, 49%). $^1$H NMR (CD$_3$OD) δ8.9 (s, 1H, DNP H-3), 8.2 (d, 1H, DNP H-5), 7.4 (d, 1H, vinyl), 7.3 (d, 2H), 7.2 (d, 1H, DNP H-6), 6.8 (d, 2H, aromatic 2,6), 6.4 (1, 1H, vinyl), 3.6 (t, 2H, CH$_2$—NH), 3.4 (t, 2H, CH$_2$—NH), 3.3 (t, 2H, CH$_2$—NH), 3.2 (t, 2H, CH$_2$—NH), 2.9 (s, 3H, methyl), 2.2-1.9 (m, 4H, CH$_2$).

EXAMPLE 5
N-α-(4-Hydroxycinnamoyl)-L-Lysine

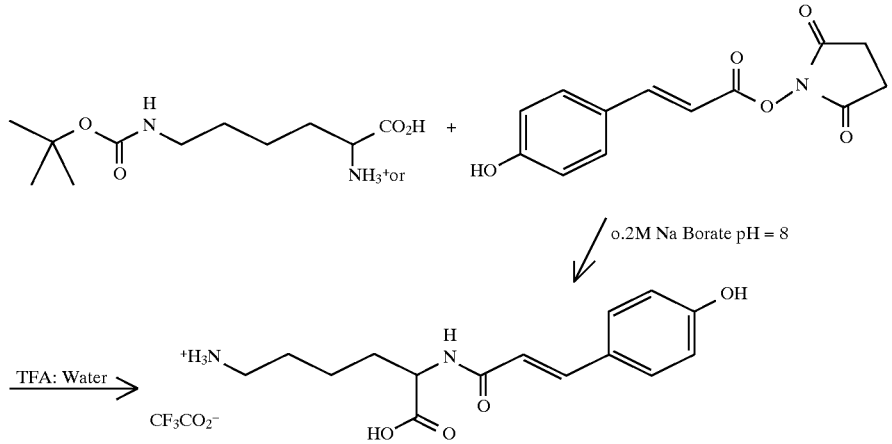

N-ε-BOC-L-lysine hydrochloride (78 mg, 0.32 mmol) is suspended in 0.2M sodium borate, pH=8 and a solution of 4-hydroxycinnamic acid, succinimidyl ester (130 mg, 0.50 mmol) in DMF (3 mL) is added in small portions with stirring. The light yellow solution is stirred at room temperature overnight and the crude reaction mixture is purified by C18 reverse phase chromatography, eluting with a linear gradient of 0–100% methanol in 50 mM sodium phosphate, pH=3.5 over 30 minutes. The major peak eluting at approximately 25 minutes is pooled from several injections and evaporated to give a glassy solid which is deprotected by stirring with trifluoroacetic acid:water (7:3) (10 mL) for 24 hours. The solution is evaporated in vacuo, stripped from toluene (3×10 mL), and triturated with ether to give 97 mg of an off white glassy solid (0.24 mmol, 75%).

EXAMPLE 6

N-ε-(5-(and-6)-Carboxyfluoresceinyl)-N-α-(4-Hydroxycinnamoyl)-L-Lysine

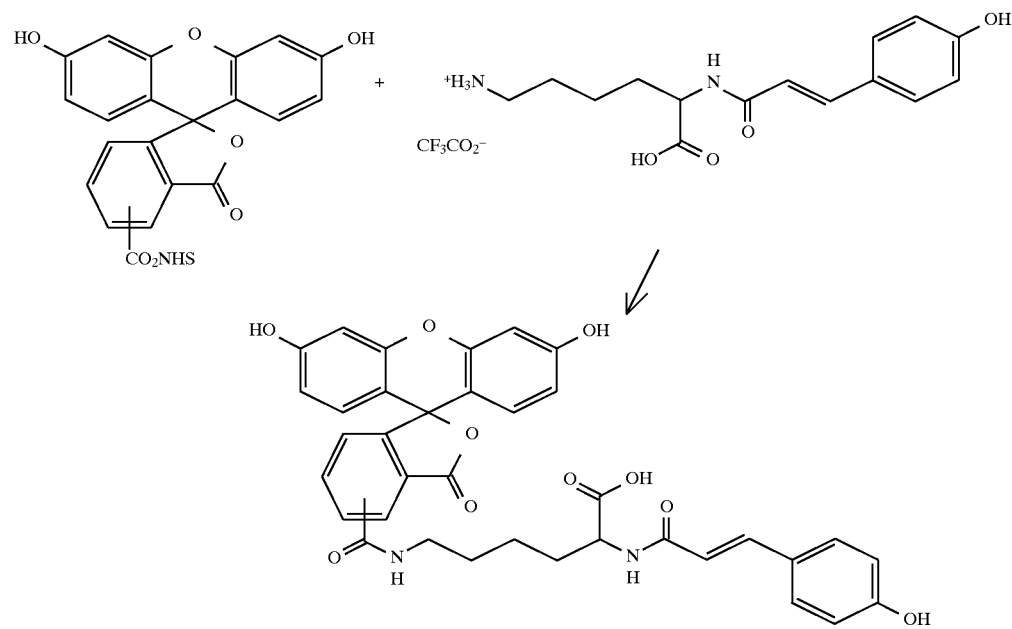

N-α-(4-Hydroxycinnamoyl)-L-lysine (24 mg, 0.06 mmol) is dissolved in water (1 mL) and the pH is adjusted to 9–10 by adding 1N NaOH. 5-(and-6)Carboxyfluorescein, N-hydroxysuccinimide ester (39 mg, 0.08 mmol) is added as a solid in several portions and the reaction mixture is stirred overnight at room temperature and purified by C18 reverse phase chromatography, eluting with a linear gradient of 0–100% methanol in 50 mM sodium phosphate, pH=3.5 over 30 minutes. The major peak is pooled from several injections to give a yellow solution containing 0.06 mmol (100%) of the desired product.

EXAMPLE 7

Detection of Cytomegalovirus (CMV) Early Antigen

CMV infected cells on a slide (eight well slides with MRC-5 cells infected with CMV, Hemagen Diagnostics, Inc.) were hydrated with phosphate buffered saline (PBS) for two minutes. An anti-CMV-horseradish peroxidase conjugate (prepared by a modification of the method of Ishikawa, E., et al., J. Immunoassay, 4, 209–237, 1983) was diluted in 0.1M tris, 0.15M NaCl, 0.5% milk protein, pH 7.5 and incubated on the slide at 37° C. for 30 minutes. The slide was then washed with 0.1M tris, 0.15M NaCl, 0.05% tween 20, pH 7.5 (TNT) buffer for two minutes. Biotinyl-tyramide (NEN Life Science Products, NEL-700) was diluted to 2 μg/ml in Amplification Diluent (NEN Life Science Products, NEL-700), added to one of the wells of the slide and incubated for 10 minutes at room temperature. N-1-Biotinyl-N-2-(4-hydroxycinnamoyl)-ethane diamine was diluted to 0.2 μg/ml in Amplification Diluent, added to a second well of the slide and incubated for 10 minutes at room temperature. The slide was washed two times for five minutes each with TNT buffer. Streptavidin-fluorescein (NEN Life Science Products, NEL-720) was diluted 1:500 in TNT buffer and incubated for 30 minutes at room temperature. The slide was washed three times for five minutes each with TNT buffer. Evans Blue (0.001%) was incubated on the slide for 1 minute, the slide was rinsed two times with deionized water and air dried. After applying anti-fade mounting media (Vectashield) and a cover slip, the slide was imaged on a Zeiss fluorescence microscope at 200X magnification.

Figure 2:
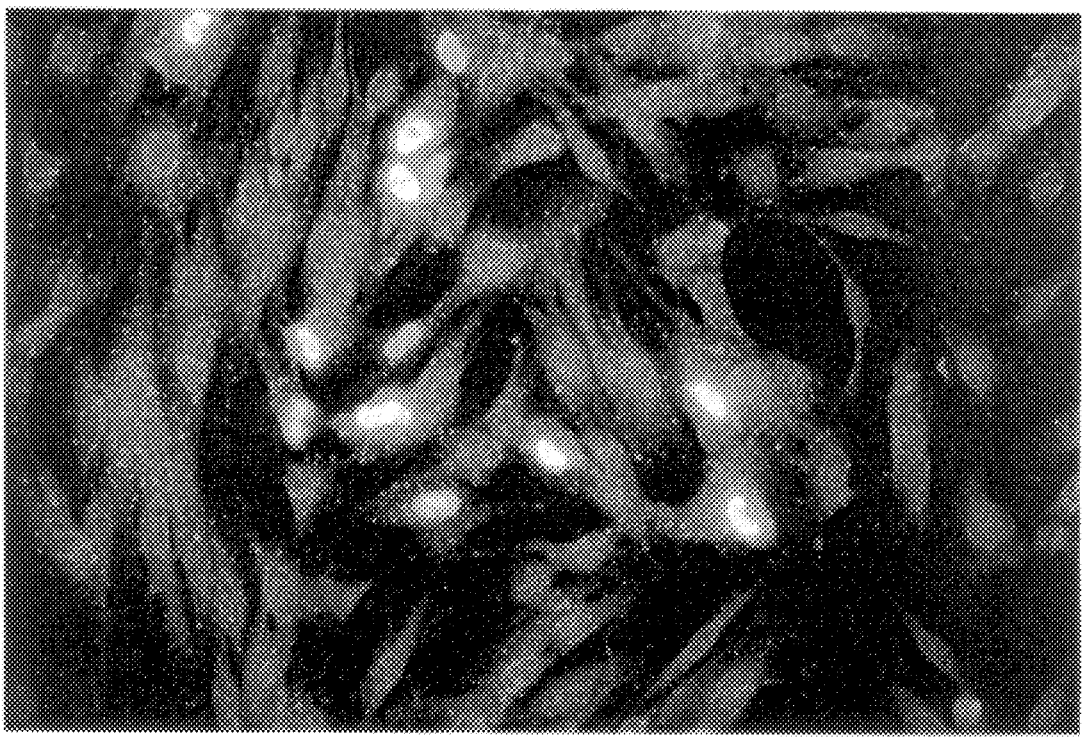
FIG. 2 shows detection of cytomegalovirus early antigen using catalyzed reporter deposition to amplify the detector signal. HRP was the ADEAS and N-1-biotinyl-N-2-(4-hydroxycinnamoyl)-ethane diamine was the conjugate. This conjugate was used at a ten-fold lower concentration than biotin tyramide.

Results: FIG. 2 demonstrates that using the substrate, N-1-Biotinyl-N-2-(4-hydroxycinnamoyl)-ethane diamine, at a ten fold lower concentration than biotinyl-tyramide results in far superior sensitivity as evidenced by the bright CMV infected nuclei. It is so sensitive, that endogenous peroxidase activity not detected by the biotinyl-tyramide amplification, is clearly detected using N-1-Biotinyl-N-2-(4-hydroxycinnamoyl)-ethane diamine. In routine practice, an endogenous peroxidase inactivation step is utilized, however, this step was not performed for this example in order to further illustrate the superior sensitivity obtained using N-1-Biotinyl-N-2(4-hydroxycinnamoyl)-ethane diamine.

What is claimed is:

1. A p-hydroxycinnamoyl-containing compound having the structure:

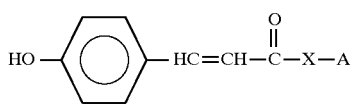

wherein:
X is a linker group, which joins A to a p-hydroxycinnamoyl moiety, and
A is a detectable label.

2. The compound according to claim 1 wherein X is selected from the group consisting of:

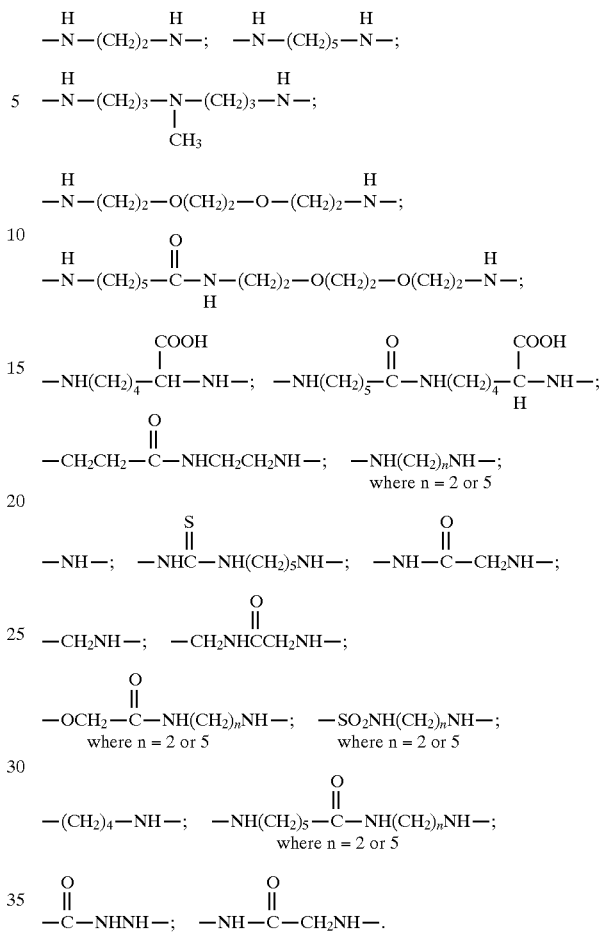

3. The compound according to claim 1 or 2 wherein A is selected from the group consisting of biotin, dinitrophenyl, fluorescein, and tetramethylrhodamine.

4. In a method for detecting or quantitating of an analyte in an assay which method comprises using an analyte dependent enzyme activation system comprising at least one enzyme to react with a conjugate comprising a detectably labeled substrate to form an activated conjugate which-covalently deposits substantially wherever there is at least one receptor for the activated conjugate, said receptor not being reactive with the analyte dependent enzyme activation system, wherein deposited detectable labels either directly or indirectly generate a signal which is detected or quantitated, the improvement comprising in combination:

reacting said analyte dependent enzyme activation system with a detectably labeled substrate having the structure of claim 1.

5. The method according to claim 4 wherein X is selected from the group consisting of:

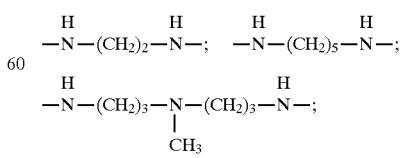

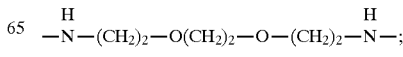

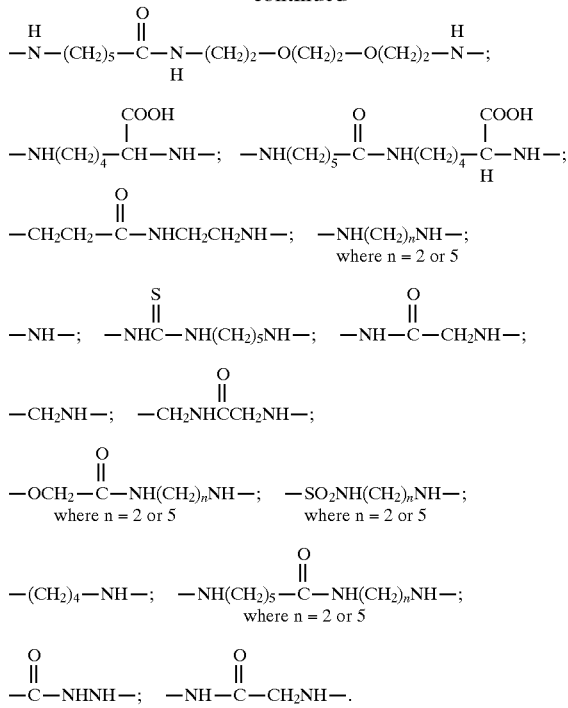

6. The method according to claim 4 or 5 wherein A is selected from the group consisting of biotin, dinitrophenyl, fluorescein, and tetramethylrhodamine.

7. The method according to claim 4 or 5 wherein the analyte dependent enzyme activation system is a peroxidase.

8. An assay for detecting or quantitating an analyte in a sample which comprises a) immobilizing the analyte on a solid phase to produce a first product;

b) reacting the first product of step (a) with an analyte-dependent enzyme activation system wherein the analyte-dependent enzyme activation system is a member of a specific binding pair coupled to an enzyme or is an enzymes, so as to produce a second product;

c) reacting the second product of step (b) with a conjugate having the structure of claim 1 to form an activated conjugate which is a first member of a specific binding pair wherein the activated conjugate deposits covalently on the solid phase by binding to the second member of the specific binding pair on the surface of the solid phase, said second member, not being reactive with the analyte dependent enzyme activation system, wherein deposited detectable labels either directly or indirectly generate a signal which is detected or quantitated; and d) detecting or quantitating the analyte in the sample from the signal generated in step (c).

9. The assay according to claim 8 wherein X is selected from the group consisting of:

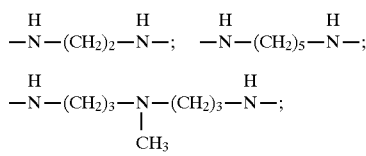

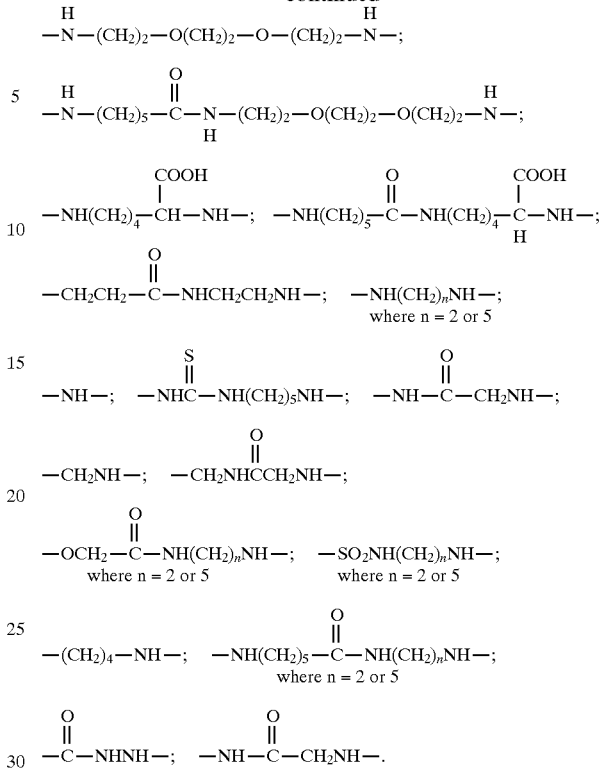

10. The assay according to claim 8 or 9 wherein A is selected from the group consisting of biotin, dinitrophenyl, fluorescein, and tetramethylrhodamine.

11. The assay according to claim 8 or 9 wherein the analyte dependent enzyme activation system is a peroxidase.

12. A method for detecting or quantitating an analyte in a sample which method comprises a) reacting an analyte which is at least one component of an analyte dependent enzyme activation system, wherein said analyte dependent enzyme activation system is a member of a specific binding pair coupled to an enzyme or is an enzyme, with a conjugate having the structure of claim 1 to form an activated conjugate, which is a first member of a specific binding pair, wherein the activated conjugate deposits on a solid phase by binding to the second member of the specific binding pair on a surface of the solid phase, said second member not being reactive with the analyte dependent enzyme activation system, wherein deposited detectable labels either directly or indirectly generate a signal which is detected or quantitated; and b) detecting or quantitating the analyte in the sample from the signal generated at step (a).

13. The assay according to claim 12 wherein X is selected from the group consisting of:

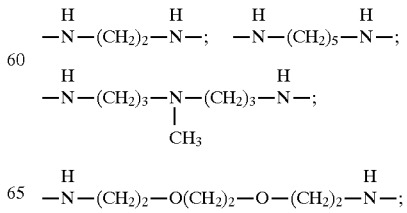

-continued

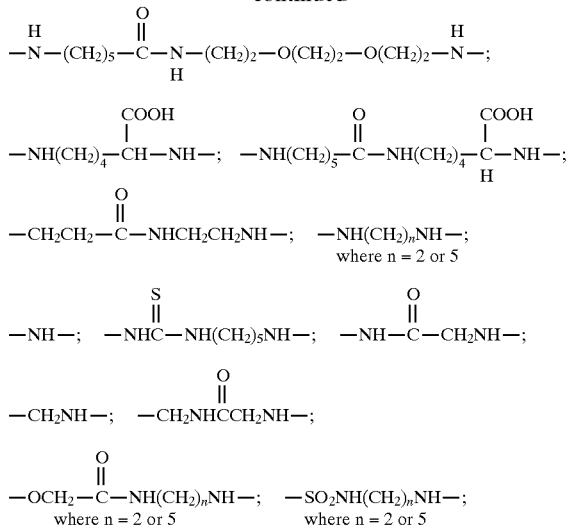

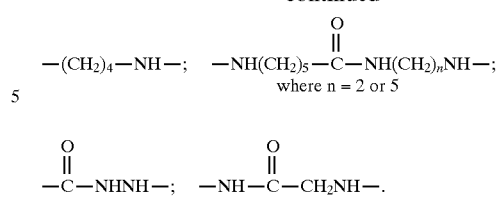

14. The assay according to claim 12 or 13 wherein A is selected from the group consisting of biotin, dinitrophenyl, fluorescein, tetramethylrhodamine.

15. The assay according to claim 12 or 13, wherein the analyte dependent enzyme activation system is a peroxidase.

16. A method for producing an activated conjugate comprising reacting a peroxidase enzyme with a detectably labeled phenol wherein the conjugate activated has the structure of claim 1.

* * * * *